United States Patent [19]

Olsen

[11] Patent Number: 4,952,618

[45] Date of Patent: Aug. 28, 1990

[54] HYDROCOLLOID/ADHESIVE COMPOSITION

[75] Inventor: Roger A. Olsen, Woodbury, Minn.

[73] Assignee: Minnesota Mining and Manufacturing Company, St. Paul, Minn.

[21] Appl. No.: 189,614

[22] Filed: May 3, 1988

[51] Int. Cl.$^5$ .................. A61L 15/00; C08L 1/00; C08L 5/02; C08L 5/04

[52] U.S. Cl. .................. 524/17; 524/24; 524/27; 524/28; 524/29; 524/45; 524/54; 524/55; 523/105; 523/111; 523/118; 128/156

[58] Field of Search .................. 524/17, 23, 24, 27, 524/29, 45, 54, 55, 28; 523/105, 111, 118; 128/156

[56] References Cited

U.S. PATENT DOCUMENTS

| | | | |
|---|---|---|---|
| 3,339,546 | 9/1967 | Chen | 128/156 |
| 3,339,549 | 9/1967 | Morse | 128/290 |
| 3,645,535 | 2/1972 | Randolph | 273/157 |
| 3,972,328 | 8/1976 | Chen | 128/156 |
| 4,192,785 | 3/1980 | Chen et al. | 128/283 |
| 4,231,369 | 11/1980 | Sorensen et al. | 128/283 |
| 4,253,460 | 3/1981 | Chen et al. | 128/283 |
| 4,394,373 | 7/1983 | Malette | 424/95 |
| 4,427,737 | 1/1984 | Cilento et al. | 428/315 |
| 4,477,325 | 10/1984 | Osburn | 204/159 |
| 4,496,357 | 1/1985 | Osburn | 604/336 |
| 4,501,835 | 2/1985 | Berke | 524/32 |
| 4,532,134 | 7/1985 | Malette et al. | 514/55 |
| 4,538,603 | 9/1985 | Pawelchak et al. | 128/156 |
| 4,539,256 | 9/1985 | Shipman | 428/315 |
| 4,551,490 | 11/1985 | Doyle et al. | 524/22 |
| 4,570,629 | 2/1986 | Widra | 128/156 |
| 4,598,004 | 7/1986 | Heinecke | 428/40 |
| 4,830,776 | 5/1989 | Thompson | 524/44 |

FOREIGN PATENT DOCUMENTS

| | | |
|---|---|---|
| 0089152 | 9/1983 | European Pat. Off. . |
| 0130061 | 2/1985 | European Pat. Off. . |
| 0152898 | 8/1985 | European Pat. Off. . |
| 2145992 | 4/1985 | United Kingdom . |

OTHER PUBLICATIONS

Chemical Patents Index, Basic Abstracts Journal, section A, week 8704, 25th Mar. 1987, No. A0775, abstract No. 87-027000/04, Derwent Publications, Ltd., London, GB; & JP-A-61 285 258 (Lion Corp.) 16-12-1986.
Chemical Patents Index, Basic Abstracts Journal, section A, week 8536, 30th Oct. 1985, No. 573, abstract No. 85-220794/36, Derwent Publications Ltd., London, GB; & JP-A-60 142 927 (Lion Corp.) 29-07-1985.

*Primary Examiner*—Nathan M. Nutter
*Attorney, Agent, or Firm*—Donald M. Sell; Walter N. Kirn; Carolyn A. Bates

[57] ABSTRACT

Hydrocolloid adhesive compositions are disclosed comprising a rubbery elastomeric base having dispersed therein hydrocolloid particles, at least some of which are polycationic hydrocolloid particles. The compositions have enhanced resistance to breakdown by body fluids and are especially useful as wound dressings.

20 Claims, 1 Drawing Sheet

HYDROCOLLOID/ADHESIVE COMPOSITION

FIELD OF THE INVENTION

This invention relates to hydrocolloid adhesive compositions having a variety of medical uses, particularly in the field of wound dressings, incontinence and ostomy care. More specifically, this invention relates to hydrocolloid adhesive compositions comprising a rubbery elastomeric base having dispersed therein one or more water soluble or water swellable hydrocolloid powders.

BACKGROUND ART

Hydrocolloid adhesive compositions have been known for many years. Chen, in U.S. Pat. No. 3,339,549 discloses a blend of a rubbery elastomer such as polyisobutylene and one or more water soluble or water swellable hydrocolloids such as a powdery mixture of pectin, gelatin and carboxymethylcellulose. The adhesive mass has a water-insoluble film applied to one surface. A composition of this type is available commercially from E. R. Squibb & Sons Inc. under the trademark "Stomadhesive" and is used as a skin barrier around stomas to prevent skin breakdown by the corrosive fluids discharged by the stoma.

In hydrocolloid adhesive compositions of this type, the polyisobutylene provides the adhesive properties and the dispersed hydrocolloid powders absorb fluid. These compositions are gaining increasing acceptance as wound dressings for dermal ulcers, burns and other exudative wounds.

One major problem which has been encountered with conventional hydrocolloid adhesive compositions is their susceptibility to breakdown upon exposure to wound exudate and body fluids. When the compositions are used as skin barriers, e.g., around stomas, absorption of fluid is desirable, but excessive swelling causes the composition to lose its moisture seal with the skin. Leakage occurs and the barrier must be replaced more often than is desirable.

Conventional hydrocolloid compositions used as wound dressings in the treatment of, for example, burns, dermal ulcers and pressure sores tend to dissolve upon exposure to wound exudate and form a gel on the surface of the wound. When the dressing is removed, a residue remains on the wound requiring removal, typically by irrigation. When this breakdown occurs the dressings may also lift off the wound and allow leakage of wound exudate onto clothing and bedding.

A number of attempts have been made to improve the integrity of hydrocolloid compositions.

U.S. Pat. Nos. 4,192,785 and 4,551,490 describe incorporating into the hydrocolloid composition a cohesive strengthening agent such as natural or synthetic fibrous material, finely divided cellulose, crosslinked dextran, crosslinked carboxymethylcellulose or a starch-acrylonitrile graft copolymer. The cohesive strengthening agent is said to control the rate of hydration of the composition thereby increasing resistance to breakdown by body fluids.

U.S. Pat. No. 4,477,325 describes incorporating into the hydrocolloid composition a mixture of a copolymer resin of ethylene and vinyl acetate (EVA). After mixing and molding, the composition is subjected to ionizing radiation to form crosslinked polymer networks of the EVA or EVA with another crosslinkable resin. The crosslinked matrix is said to provide controlled swelling.

U.S. Pat. No. 4,496,357 describes the incorporation of fumed silica into hydrocolloid compositions to control swelling.

Generally speaking, these prior methods of improving the integrity of hydrocolloid dressings all involve crosslinking or otherwise strengthening the matrix of the composition to control swelling upon contact with body fluids. This approach tends to limit the absorption capacity of the composition, which is not always desirable, particularly when the composition is used as a wound dressing on highly exudative wounds.

SUMMARY OF THE INVENTION

According to the present invention the integrity of hydrocolloid adhesive compositions is improved through the judicious selection of the hydrocolloid particles used in the compositions. There is provided a pressure-sensitive adhesive composition comprising a rubbery elastomer having dispersed therein water absorbable or water swellable hydrocolloid particles wherein at least some of the hydrocolloid particles are polycationic hydrocolloid particles. Compositions of the invention have an absorbency value (hereinafter defined) of at least 180 percent and an integrity value (hereinafter defined) of at least 60 percent. The polycationic hydrocolloid particles preferably comprise at least 10 percent by weight of the composition. The total amount of hydrocolloid particles preferably comprises at least 20 percent by weight of the composition. For wound healing applications, greater absorbency is generally required and a total hydrocolloid concentration of at least 40 percent by weight is preferred.

Preferred compositions of the invention contain a mixture of hydrocolloid particles, including polycationic and polyanionic hydrocolloid particles. Especially preferred mixtures comprise polycationic, polyanionic and neutral hydrocolloid particles in approximately equal proportions.

The preferred polycationic hydrocolloid for use in the compositions of the invention is a water soluble chitosan salt such as chitosan malate or chitosan glutamate. Especially preferred polyanionic and neutral hydrocolloid particles comprise pectin and gelatin, respectively.

When the hydrocolloid compositions of the invention are used for wound healing, it is preferred to cover one surface of the composition with a backing which is preferably moisture vapor permeable.

Compositions of the invention exhibit greater resistance to biological fluids than comparable hydrocolloid adhesive compositions of the prior art which do not contain polycationic hydrocolloid particles. Wound dressings made from compositions of the present invention exhibit lower rates of wound exudate leakage during use than dressings made from such prior art compositions. Longer wear time is provided and less clean up is required upon removal of the dressing since less residue is left in the wound bed.

Compositions of the present invention provide surprisingly increased integrity without a concomitant decrease in absorbency. In fact, because the compositions maintain their integrity longer, they are actually able to absorb more fluid over extended periods of time than comparable prior art compositions without polycationic hydrocolloid particles.

In addition to increased integrity and resistance to breakdown by body fluids, preferred compositions of the present invention containing chitosan particles exhibit antimicrobial properties, and may also exhibit hemostatic, immunopotentiating, endotoxin binding and enhanced wound healing properties.

DETAILED DESCRIPTION

The hydrocolloid adhesive compositions of the present invention comprise a blend of at least two basic ingredients, viz., the rubbery elastomeric adhesive matrix and the powdery polycationic hydrocolloid. In most cases, the polycationic hydrocolloid powder will be mixed with other hydrocolloid powders to provide optimum results in terms of absorbency and integrity.

Materials for forming the rubbery elastomeric adhesive matrix are well known and described, for example, in U.S. Pat. Nos. 3,339,546 and 4,253,460. Both natural or synthetic rubber or mixtures thereof are useful, also Kratons (block copolymers of styrene/butadiene and the like available from Shell Chemical Company), polybutene and polyacrylates may be used. Tackifiers, plasticizers and other materials known in the art for incorporation in the rubbery elastomeric matrix may also be used (See, for example, U.S. Pat. Nos. 4,231,369 and 4,551,490). Polyisobutylene is particularly useful as the rubbery elastomeric matrix. Preferably, the polyisobutylene is a mixture of low molecular weight polyisobutylene (viscosity average molecular weight of about 10,000 to 12,000) and a higher molecular weight polyisobutylene (viscosity average molecular weight of about 80,000 to 100,000) in a ratio of about four to one. Suitable low and high molecular weight polyisobutylene pressure sensitive adhesives are available from Exxon Chemical Company under the tradenames Vistanex LM and Vistanex L-100, respectively.

The rubbery elastomer preferably comprises about 30 to 50 percent by weight of those compositions used as wound dressings, and as much as 80 percent by weight of compositions used for ostomy care and related applications. When the elastomer is present in amounts below about 35 percent, the composition tends to exhibit inadequate adhesive properties. For wound dressing applications, it is desirable to minimize the amount of elastomer present, consistent with achieving adequate adhesive properties, in order to maximize the level of hydrocolloid, thereby achieving maximum fluid absorbency.

The improvement in integrity associated with the compositions of the present invention is attributable to the polycationic hydrocolloid particles contained in the compositions, particularly when mixed with anionic hydrocolloid particles or a blend of anionic and neutral hydrocolloid particles. The polycationic hydrocolloid is preferably a chitosan salt. Water soluble salts of chitosan, such as chitosan malate or chitosan glutamate are especially preferred. Improved composition integrity has also been observed with the polycationic hydrocolloid DEAE-Dextran. Other polycationic hydrocolloids which may be useful include any cationic-substituted hydrocolloid.

The polycationic hydrocolloid preferably comprises at least 30 percent of all hydrocolloids present, and in the case of wound dressing applications, should comprise at least 10, and preferably between 15 and 25, percent by weight of the total composition. Examples of other hydrocolloids which may be included in the compositions are neutral hydrocolloids such as gelatin, locust bean gum and guar gum, and polyanionic hydrocolloids such as pectin, carboxymethylcellulose, alginate, carageenan, xanthan gum, tragacanth gum, or mixtures of neutral and polyanionic hydrocolloids. The best results are obtained with a mixture of gelatin, chitosan malate and pectin.

The amount of hydrocolloid present in the composition for wound healing applications is preferably as large as possible consistent with maintaining adequate adhesive properties. This amount has been found to be about 60 percent by weight of the compositions. For other applications, e.g., skin barriers, concentrations as low as 20 may be useful.

Compositions of the invention may also contain minor amounts of other ingredients such as antioxidants, deodorants, perfumes, antimicrobials and other pharmacologically active agents as is well known in the art.

Compositions of the invention are made by compounding the pressure sensitive adhesive and any thermoplastic elastomer with a heavy duty mixer until a homogeneous blend is obtained. Small portions of a dry-blended premix of hydrocolloid particles are added and milling continued until a homogeneous dispersion of the particles in the adhesive phase is obtained. The blended adhesive mass is then molded into sheets for further conversion into wound dressings or formed into shapes such as strips, rings, etc., by any number of means commonly used for converting plastics and elastomers into shapes such as compression or injection molding.

The compositions are preferably sterilized by gamma irradiation at between 2.5 and 4 MRad. Ethylene oxide and E-Beam irradiation may also be used.

The invention is further illustrated by reference to the accompanying drawings wherein like reference numerals refer to like elements.

DESCRIPTION OF THE DRAWINGS

Referring to FIGS. 1 and 2, wound dressing 10 comprises an oval-shaped sheet 12 of the hydrocolloid adhesive composition of the present invention. Laminated to the top side (side facing away from the skin when the dressing is in use) is a slightly larger oval-shaped transparent film backing 14. An intermediate layer 16 of a conventional pressure-sensitive skin adhesive is used to facilitate lamination. The peripheral portion of the film backing 14 and adhesive layer 16 extends beyond the hydrocolloid sheet 12 to assist in adhering the hydrocolloid sheet 12 to the skin. A conventional release liner 18 is used to protect the exposed surface of the hydrocolloid sheet 12 and the exposed portion of the adhesive layer 16 prior to use. Delivery sheet 20 is attached to the top side of film backing 14 to prevent wrinkling and curling of the edges of backing 14 and adhesive layer 16 after removal of release liner 18. Delivery sheet 20 is divided into two sections of approximately equal size and heat-sealed to the top side of film backing 14. Both sections have a non-heat-sealed edge 22 at the center of the dressing to form handles which facilitate grasping and removal of the delivery sheet. Delivery sheet 20 supports the exposed periphery of backing 14 and adhesive layer 16 during application of the dressing to the patient. Once the dressing is in place on the skin, delivery sheet 20 is removed.

Figure 1:
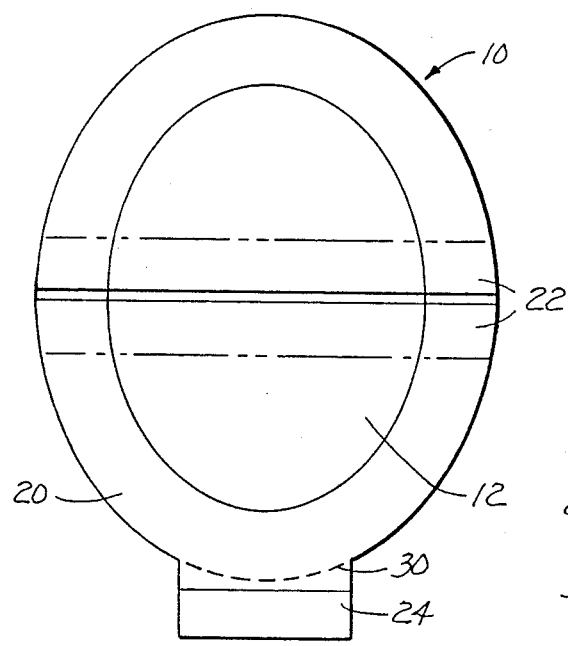
FIG. 1 is a top view of a wound dressing incorporating the hydrocolloid adhesive composition of the present invention.

Separation of the release liner 18 from the hydrocolloid sheet 12 and adhesive layer 16 of the dressing 10 is facilitated by two tabs 24 and 26. Tab 24 comprises aligned rectangularly-shaped extensions of each of the delivery sheet 20, film backing 14 and adhesive layer 16, and further comprises a stiffening member 28 adhered to the adhesive layer 16 to facilitate separation of the tab members from each other. The second tab 26 is aligned with tab 24 and comprises a rectangularly-shaped extension of release liner 18. A perforation line 30 separates tab 24 from the main oval section of the dressing. Tab 24 provides an area for the person applying the dressing to hold onto without touching or otherwise contaminating the adhesive 14 and hydrocolloid sheet 12 in the main oval portion of the dressing. After the dressing is in place on the patient, tab 24 can be separated from the main oval portion of the dressing along perforation line 30.

Figure 2:
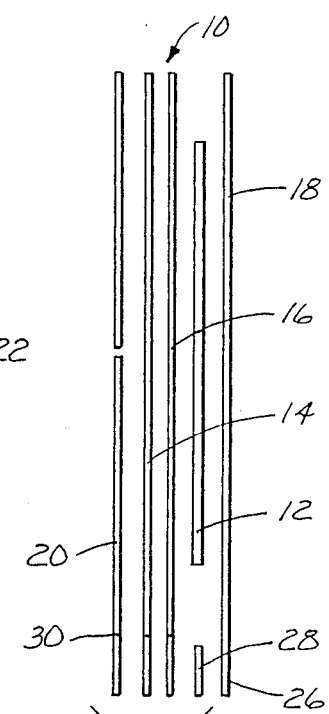
FIG. 2 is an exploded side view of the dressing of FIG. 1.

The dressing illustrated in FIGS. 1 and 2 is the presently preferred embodiment of the invention. The oval shape reduces dressing size and minimizes edge lift.

The film backing 14 is preferably a highly moisture vapor permeable film of, for example, porous polyethylene such as that disclosed in U.S. Pat. No. 4,539,256 or polyurethane such as that described in U.S. Pat. Nos. 3,645,535 or 4,598,004. Moisture vapor permeable films of this type allow the wound exudate to evaporate through the dressing and reduce the pooling of exudate under the dressing. The moisture vapor transmission rate of the backing is preferably at least 500 grams/square meter/24 hours when measured at 40° C. and 80 percent humidity differential. Film backing 14 is preferably about 1 mil (0.0256 mm) thick.

Adhesive layer 16 is also preferably moisture vapor permeable so as not to detract significantly from the moisture vapor permeability of the film backing 14. Suitable medical adhesives of this type such as the copolymer acrylate adhesive and polyvinyl ether adhesive described in U.S. Pat. Nos. 4,598,004 and 3,645,535, respectively, are well known. The adhesive is preferably about 1-3 mils (0.025-0.075 mm) thick.

Delivery sheet 22 is preferably a polyester-film with a polyethylene-ethylvinyl acetate heat seal coating available commercially from 3M, under the trademark Scotchpack 1220.

Hydrocolloid sheet 12 preferably has the composition of Example 14 below and has a thickness between 40 and 70 mils (1.0-1.75 mm).

Figure 3:
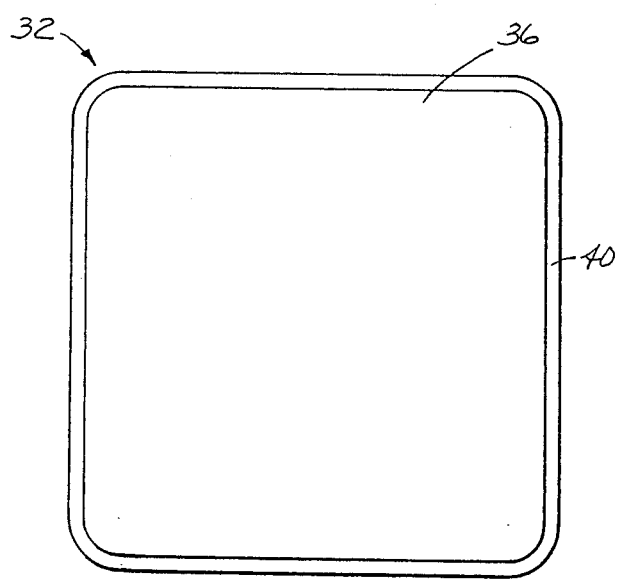
FIG. 3 is a top view of an alternative embodiment of a wound dressing incorporating the hydrocolloid adhesive composition of the present invention.
Figure 4:
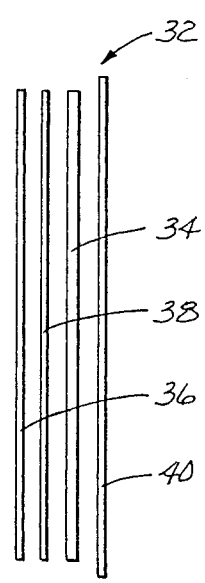
FIG. 4 is an exploded side view of the dressing of FIG. 3.

The dressing of FIGS. 3 and 4 represents an alternative embodiment of a wound dressing which incorporates the hyrocolloid adhesive composition of the present invention. Dressing 32 comprises a square sheet 34 of the hydrocolloid adhesive composition. A square film backing 36 of the same dimensions as the hydrocolloid sheet is laminated to the top surface (facing away from the skin) of the hydrocolloid sheet by adhesive layer 38. Release liner 40 covers the exposed surface of hydrocolloid sheet 34 and extends outwardly from the hydrocolloid sheet on all sides to facilitate grasping of the liner 40 and removal thereof prior to application of the dressing to the wound. The materials which can be used to form film backing 34 and adhesive layer 38 are essentially the same as those discussed above in connection with the embodiment of FIGS. 1 and 2. The dressing of FIG. 3 is cheaper to manufacture than the dressing of FIG. 1 and is also easier to cut to the dimensions of the wound.

The hydrocolloid adhesive compositions of the present invention exhibit increased integrity over similar prior art compositions without a polycationic hydrocolloid. Generally speaking, compositions of the invention also exhibit increased absorbency over such prior art compositions. The integrity and absorbency of the compositions were determined according to the following test procedures.

INTEGRITY TEST

Preweighed($W_i$) test samples of the dressing 2.54 cm×2.54 cm) are placed in an eight ounce bottle containing fifty milliliters of phosphate buffered saline solution (pH 7.4) available from Sigma Chemical Company. The bottles are capped and agitated on a bottle roller at 50 rpms for a period of eighteen hours. The test sample is removed, weighed, dried in a circulating air oven maintained at 100° C. and 10 percent relative humidity until dry (4–6 hours) and weighed($W_f$).

The Integrity Value of the sample is calculated using the following equation:

$$\text{Integrity Value} = \frac{W_f}{W_i} \times 100$$

Compositions of this invention exhibit an Integrity Value of at least 60 percent and preferably 80 percent.

ADSORPTION TEST

Preweighed($W_i$) test samples (2.54 cm×2.54 cm) of the dressing are placed in an eight ounce bottle containing fifty milliliters of phosphate buffered (pH 7.4) saline solution available from Sigma Chemical Company. The bottles are capped and allowed to stand without agitation. Test samples are removed at two hour intervals, weighed($W_t$) and returned to the bottle. The Absorbency Value is calculated using the following formula:

$$\text{Absorbency Value} = \frac{W_t - W_i}{W_i} \times 100$$

Twenty-four hour absorbency data is reported for the dressing compositions listed in Table 1 below. Compositions of the present invention exhibit a twenty-four hour absorbency value of at least 180 percent and preferably 300 percent.

EXAMPLES 1–3, 10–21 and 29 AND COMPARATIVE EXAMPLES 4–9 and 22–28

Wound dressings incorporating the hydrocolloid adhesive compositions of the invention and comparative dressings (Examples 4–9 and 22–28) as identified in Table I below were made according to the same general procedure.

The adhesive phase of the dressing was prepared by compounding a mixture of the pressure sensitive material and a thermoplastic elastomer on a two-roll rubber mill without supplemental heating or cooling until a homogeneous blend of the two components was obtained (typically 1–2 minutes). Small portions of a blended premix of the hydrocolloid powders, which had been previously prepared by dry blending the powders in the specified weight ratios, were then added to the adhesive phase and the milling continued until a homogeneous dispersion of the powders in the adhesive phase obtained. The blended adhesive mass was then removed from the rubber mill and formed into approximately 60 mil (1.5 mm) thick sheet stock material by compression molding the adhesive mass at approximately 150° C. and approximately 2,000 psi between two sheets of silicone release paper. The release paper was removed from one side of the adhesive sheet stock and replaced with a backing material, preferably a high moisture vapor permeable polyurethane film having a pressure sensitive adhesive on the surface contacting the adhesive stock, e.g., Tegaderm Transparent Dressing manufactured by 3M. The resulting laminate structure was then die cut into the desired shapes and sterilized by exposure to gamma radiation.

TABLE 1

Examples 1-29

| | \multicolumn{17}{c|}{Example Number} |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Adhesive Matrix | | | | | | | | | | | | | | | | | |
| Vistanex LM-MH[1] | 32 | 32 | 32 | 32 | 32 | 32 | 32 | 32 | 32 | 32 | 32 | 32 | 32 | 32 | 32 | 32 | 32 |
| Vistanex L-100[2] | 8 | 8 | 8 | 8 | 8 | 8 | 8 | 8 | 8 | 8 | 8 | 8 | 8 | 8 | 8 | 8 | 8 |
| Hydrocolloid Neutral | | | | | | | | | | | | | | | | | |
| Gelatin[3] | 40 | 20 | — | 20 | 20 | — | 20 | 20 | 20 | 20 | 20 | 20 | 20 | 20 | 20 | 20 | 20 |
| Locust Bean Gum[4] | — | — | — | — | — | — | — | — | — | — | — | — | — | — | — | — | — |
| Guar Gum[5] | — | — | — | — | — | — | — | — | — | — | — | — | — | — | — | — | — |
| Polyanion | | | | | | | | | | | | | | | | | |
| Pectin[6] | — | — | — | 20 | — | 30 | 20 | 20 | 20 | — | — | — | 20 | 20 | — | — | — |
| Na CMC[7] | — | — | — | — | 20 | 30 | 20 | 20 | — | 20 | 20 | — | — | — | — | — | — |
| Na Alginate[8] | — | — | — | 20 | 20 | — | — | — | — | — | — | 20 | — | — | — | — | — |
| Carageenan[9] | — | — | — | — | — | — | — | — | — | — | — | — | — | — | 20 | — | — |
| Xanthan Gum[10] | — | — | — | — | — | — | — | — | — | — | — | — | — | — | — | 20 | — |
| Tragacanth Gum[11] | — | — | — | — | — | — | — | — | — | — | — | — | — | — | — | — | 20 |
| Aqualon C[12] | — | — | — | — | — | — | — | — | — | — | — | — | — | — | — | — | — |
| Polycation | | | | | | | | | | | | | | | | | |
| Chitosan Malate[13] | 20 | 40 | 60 | — | — | — | — | — | — | — | 20 | 20 | 20 | — | 20 | 20 | 20 |
| Chitosan Glutamate[14] | — | — | — | — | — | — | — | — | — | — | — | — | — | 20 | — | — | — |
| Chitosan Lactate[15] | — | — | — | — | — | — | — | — | — | — | — | — | — | — | — | — | — |
| DEAE - Dextran[16] | — | — | — | — | — | — | — | — | 20 | 20 | — | — | — | — | — | — | — |
| Percent Integrity# | 92 | 80 | 70 | 36 | 10 | 5 | 19 | 45 | 82 | 92 | 85 | 69 | 93 | 85 | 89 | 92 | 76 |
| Absorbency | 180 | 270 | 310 | 390 | 160 | 270 | 240 | 320 | 110 | 240 | 490 | 390 | 360 | 370 | 330 | 350 | 320 |

| | \multicolumn{12}{c|}{Example Number} |
|---|---|---|---|---|---|---|---|---|---|---|---|---|
| | 18 | 19 | 20 | 21 | 22 | 23 | 24 | 25 | 26 | 27 | 28 | 29 |
| Adhesive Matrix | | | | | | | | | | | | |
| Vistanex LM-MH[1] | 32 | 32 | 32 | 32 | 32 | 32 | 32 | 32 | 32 | 32 | 32 | 32 |
| Vistanex L-100[2] | 8 | 8 | 8 | 8 | 8 | 8 | 8 | 8 | 8 | 8 | 8 | 8 |
| Hydrocolloid Neutral | | | | | | | | | | | | |
| Gelatin[3] | — | — | — | 20 | — | 20 | 20 | 20 | — | — | 20 | 20 |
| Locust Bean Gum[4] | — | 20 | — | — | — | — | — | — | — | 30 | 20 | — |
| Guar Gum[5] | 20 | — | — | — | — | — | — | — | 30 | — | — | 20 |
| Polyanion | | | | | | | | | | | | |
| Pectin[6] | 20 | 20 | 20 | 10 | 30 | 20 | 20 | 20 | — | — | — | — |
| Na CMC[7] | — | — | — | — | — | 5 | 10 | 15 | — | — | — | — |
| Na Alginate[8] | — | — | 20 | 10 | 30 | — | — | — | — | — | — | — |
| Carageenan[9] | — | — | — | — | — | — | — | — | — | — | — | — |
| Xanthan Gum[10] | — | — | — | — | — | — | — | — | — | — | — | — |
| Tragacanth Gum[11] | — | — | — | — | — | — | — | — | — | — | — | — |
| Aqualon C[12] | — | — | — | — | — | 15 | 10 | 5 | — | — | — | — |
| Polycation | | | | | | | | | | | | |
| Chitosan Malate[13] | 20 | 20 | 20 | 20 | — | — | — | — | 30 | 30 | 20 | 20 |
| Chitosan Glutamate[14] | — | — | — | — | — | — | — | — | — | — | — | — |
| Chitosan Lactate[15] | — | — | — | — | — | — | — | — | — | — | — | — |
| DEAE - Dextran[16] | — | — | — | — | — | — | — | — | — | — | — | — |
| Percent Integrity# | 90 | 96 | 89 | 89 | 0 | 0 | 0 | 0 | 55 | 30 | 0 | 80 |

TABLE 1-continued

Examples 18-29

| | | | | | | | | | | | | |
|---|---|---|---|---|---|---|---|---|---|---|---|---|
| Absorbency | 360 | 370 | 360 | 360 | 220 | 500 | 500 | 520 | 245 | —* | 370 | 280 |

Average of three replicate tests
*Hydrocolloid adhesive dissolved off backing
[1]Polyisobutylene PSA available from Exxon Chemical Co., Viscosity average MW 10,000-11,700
[2]Polyisobutylene rubber available from Exxon Chemical Co., Viscosity average MW 81,000-99,000
[3]Gelatin 150 Bloom A available from Atlantic Gelatin
[4]Available from Sigma Chemical Co.
[5]Available from Sigma Chemical Co.
[6]Pectin USP-100 available from Hercules, Inc.
[7]Cellulose Gum CMC #7H4XF available from Hercules, Inc.
[8]Protanal SF 40 available from Proton Laboratories
[9]Caregeenan type II, available from Sigma Chemical Co.
[10]Available from Sigma Chemical Co.
[11]Available from Sigma Chemical Co.
[12]Available from Hercules, Inc.
[13]Available from Protan Laboratories
[14]Available from Protan Laboratories
[15]Available from Protan Laboratories
[16]Available from Sigma Chemical Co.

Examination of the Integrity data generated for the samples reported in Table 1 shows that, in general, better integrity was obtained from compositions containing a polycationic hydrocolloid than from compositions without a polycationic hydrocolloid. Compositions containing a mixture of hydrocolloids including both polycationic and polycationic hydrocolloids, generally exhibit the best integrity. Example 13, which represents an optimized formulation for the dressings of the present invention, gives approximately double the integrity obtained from the dressing of Example 8 which has a composition similar to that used in a commercially available hydrocolloid dressing. (DuoDerm Hydroactive Dressing from E. R. Squibb & Sons, Inc.)

The absorbency of the dressing compositions, especially when considered in conjunction with the integrity data, further illustrates the improvement which the dressings of the present invention offer. Generally speaking, high absorbencies at 24 hours can be realized with dressing compositions based on mixtures of hydrocolloids which do not include polycationic hydrocolloids, but only at the expense of the integrity of the dressing. As such dressings lose integrity over time, absorbency is decreased. The preferred formulation for dressings of the present invention (Example 13) when compared to the DuoDerm product, did not show a significant difference in absorbency at 24 hours, but at 48 hours the composition of Example 13 showed a twofold increase in absorbency. This increase in absorbency is directly related to the increased integrity of the composition of Example 13 over the Duoderm product. The actual results of the comparative study are shown in the following table.

TABLE 2

| | Absorbency (%) | | | | | | |
|---|---|---|---|---|---|---|---|
| | Hours | | | | | | |
| Composition | 2 | 4 | 6 | 8 | 23 | 48 | 72 | 144 |
| Example 13 | .97 | 1.55 | 2.04 | 2.40 | 3.60 | 5.26 | 5.29 | 5.54 |
| DuoDerm | 1.36 | 2.06 | 2.44 | 2.59 | 3.19 | 2.18 | 1.23 | 1.12 |

| | Integrity (%) | | | | | |
|---|---|---|---|---|---|---|
| | Hours | | | | | |
| Composition | 6 | 24 | 32 | 40 | 48 | 120 |
| Example 13 | 94.6 | 89.0 | 95.0 | 95.0 | 92.0 | 87.0 |
| DuoDerm | 90.6 | 45.0 | 37.0 | 29.0 | 23.0 | 18.0 |

EXAMPLE 27

The dressing composition of Example 13 was scaled up in an extrusion process as follows:

A hydrocolloid adhesive premix was prepared by compounding gelatin (25 weight percent) in Vistanex L-100 (75 weight percent) on a two roll mill with no supplemental heating or cooling until a homogeneous mixture was obtained (approximately 15 minutes). The premix was removed from the mill and cut into cubes approximately 2.54 cm×2.54 cm×2.54 cm.

A mixture of chitosan malate (1.87 parts), pectin (1.87 parts), gelatin (1.62 parts) and the previously described hydrocolloid adhesive premix (1 part) were charged into a 10 gallon Baker-Perkins double arm sigma blade mixer (mogul) and the mixture blended for two (2) minutes. The mogul was stopped, Vistanex LM-MH charged to the mogul (3.00 parts) and the mixture blended for an additional nine (9) minutes. The blended hydrocolloid adhesive (HCA), which had a final composition of 20 weight percent chitosan malate, 20 weight percent pectin, 20 weight percent gelatin, 8 weight percent Vistanex L-100 and 32 weight percent Vistanex LM-MH, was removed from the mogul and cut into strips prior to being fed into a 3.5 inch Davis-Standard Rubber Extruder to convert it into a sheet stock form. The HCA was cold-fed into the extruder and heated to about 70° C. as it was pumped to the extrusion die. The HCA was extruded into a nip roller assembly having a silicone release liner (Grade 8766 semi-bleached paper, 60#, coated on both sides, available from James River Corp., H. P. Smith Division) over the top roll and the product liner (2-6OBKG-157 and 99AM, silicone coated on both sides, available from Daubert Chemical Co.) over the bottom roll. The release liner was removed from the laminate construction and the HCA/product liner construction wound into 100 meter storage rolls. The HCA layer produced by this process was approximately 1.5 mm thick. Dressings of the present invention are prepared by laminating the HCA/product liner to a high moisture vapor permeable bandage such as that described in U.S. Pat. No. 4,499,896. The lamination is effected by assembling a construction having the adhesive component of the bandage in contact with the HCA component of the HCA/product liner laminate and passing the construction through a heated nip roll assembly.

What is claimed is:

1. A pressure sensitive adhesive composition comprising a rubbery elastomer having dispersed therein water absorbable or swellable hydrocolloid particles wherein at least some of said hydrocolloid particles are polycationic hydrocolloid particles, said composition having an Integrity Value of at least 60 percent and an Absorbency Value of at least 180 percent.

2. The adhesive composition of claim 1 wherein said polycationic hydrocolloid is selected from the group consisting of a chitosan salt, DEAE Dextran and mixtures thereof.

3. The adhesive composition of claim 2 wherein said polycationic hydrocolloid is a water-soluble chitosan salt.

4. The adhesive composition of claim 1 wherein said hydrocolloid particles comprise at least one polyanionic hydrocolloid.

5. The adhesive composition of claim 4 further comprising a neutral hydrocolloid.

6. The adhesive composition of claim 5 wherein said neutral hydrocolloid is gelatin.

7. The adhesive composition of claim 4 wherein said polyanionic hydrocolloid is selected from the group consisting of pectin, sodium carboxymethylcellulose and mixtures thereof.

8. The adhesive composition of claim 6 wherein the polycationic hydrocolloid is a chitosan salt and said polyanionic hydrocolloid is pectin.

9. The adhesive composition of claim 1 wherein said polycationic hydrocolloid is present in an amount between 15 and 25 percent by weight of the adhesive composition.

10. The adhesive composition of claim 1 wherein said rubbery elastomer is polyisobutylene.

11. The composition of claim 10 wherein said polyisobutylene comprises at least 30 percent by weight of said adhesive composition.

12. A pressure sensitive adhesive composition comprising a rubbery elastomer having dispersed therein at least 10 percent by weight of a polycationic hydrocolloid powder and at least 10 percent by weight of polyanionic hydrocolloid or a mixture of polyanionic and neutral hydrocolloids.

13. The composition of claim 12 comprising about 20 percent by weight of a water soluble chitosan salt and about 40 percent by weight of a polyanionic hydrocolloid or a mixture of polyanionic and neutral hydrocolloids.

14. The composition of claim 1 having an integrity value of at least 85 percent and an absorbency value of at least 300 percent.

15. A wound dressing comprising a sheet of the composition of claim 1 and a moisture vapor permeable backing covering one major surface of said sheet.

16. The wound dressing of claim 15 wherein said backing is a transparent film.

17. The wound dressing of claim 16 wherein said film comprises polyurethane or porous polyethylene.

18. The wound dressing of claim 15 wherein said sheet and backing are oval shaped, said backing extends beyond the periphery of the sheet on all sides and said backing contains a pressure sensitive adhesive on at least the portion of the lower surface of the backing extending beyond said sheet.

19. The wound dressing of claim 18 further comprising a removable delivery sheet attached to the surface of said backing opposite that attached to said sheet.

20. A method of treating a wound comprising applying to the wound the composition of claim 1.

* * * * *

UNITED STATES PATENT AND TRADEMARK OFFICE
CERTIFICATE OF CORRECTION

PATENT NO. : 4,952,618

DATED : August 28, 1990

INVENTOR(S) : Roger A. Olsen

It is certified that error appears in the above-identified patent and that said Letters Patent is hereby corrected as shown below:

Col. 3, line 13, "oases" should read --cases--.

Col. 9, line 11, "Proton" should read --Protan--.

Signed and Sealed this

Twenty-ninth Day of September, 1992

Attest:

DOUGLAS B. COMER

*Attesting Officer*   *Acting Commissioner of Patents and Trademarks*